United States Patent
Baur et al.

(10) Patent No.: US 7,723,268 B2
(45) Date of Patent: May 25, 2010

(54) USE OF ALCOHOL ETHOXYLATES AS PENETRATION ENHANCERS

(75) Inventors: Peter Baur, Eppstein (DE); Dieter Feucht, Eschborn (DE); Mathias Kremer, Burscheid (DE); Frederic Top, Leverkusen (DE); Ulrich Schwiedop, Monheim (DE); Arndt Wellmann, Kürten (DE)

(73) Assignee: Bayer Cropscience AG, Monheim (DE)

( * ) Notice: Subject to any disclaimer, the term of this patent is extended or adjusted under 35 U.S.C. 154(b) by 869 days.

(21) Appl. No.: 10/501,434

(22) PCT Filed: Jan. 7, 2003

(86) PCT No.: PCT/EP03/00053

§ 371 (c)(1),
(2), (4) Date: Nov. 17, 2004

(87) PCT Pub. No.: WO03/059066

PCT Pub. Date: Jul. 24, 2003

(65) Prior Publication Data

US 2005/0070440 A1 Mar. 31, 2005

(30) Foreign Application Priority Data

Jan. 16, 2002 (DE) ................ 102 01 391

(51) Int. Cl.
*A01N 43/653* (2006.01)
(52) U.S. Cl. ................ 504/273; 504/272
(58) Field of Classification Search ................ 504/100, 504/273
See application file for complete search history.

(56) References Cited

U.S. PATENT DOCUMENTS

| 3,884,910 | A | * | 5/1975 | Pilgram | 548/263.8 |
|---|---|---|---|---|---|
| 4,351,753 | A | * | 9/1982 | Kaneko | 516/71 |
| 5,057,144 | A | | 10/1991 | Daum et al. | 71/92 |
| 5,085,684 | A | * | 2/1992 | Muller et al. | 504/273 |
| 5,094,683 | A | | 3/1992 | Daum et al. | 71/94 |
| 5,149,356 | A | | 9/1992 | Müller et al. | 71/90 |
| 5,241,074 | A | | 8/1993 | Daum et al. | 548/263.8 |
| 5,276,162 | A | | 1/1994 | Müller et al. | 548/263.4 |
| 5,300,480 | A | | 4/1994 | Haas et al. | 504/273 |
| 5,405,970 | A | | 4/1995 | Daum et al. | 548/263.6 |
| 5,488,028 | A | | 1/1996 | Haas et al. | 504/193 |
| 5,532,378 | A | | 7/1996 | Daum et al. | 548/263.8 |
| 5,534,486 | A | | 7/1996 | Müller et al. | 504/273 |
| 5,541,337 | A | | 7/1996 | Müller et al. | 548/263.6 |
| 5,554,761 | A | | 9/1996 | Haas et al. | 548/263.6 |
| 5,597,939 | A | | 1/1997 | Müller et al. | 558/8 |
| 5,625,074 | A | | 4/1997 | Daum et al. | 548/263.8 |
| 5,631,380 | A | | 5/1997 | Haas et al. | 548/263.4 |
| 5,652,372 | A | | 7/1997 | Müller et al. | 548/263.4 |
| 5,750,718 | A | | 5/1998 | Müller et al. | 548/263.6 |
| 5,869,681 | A | | 2/1999 | Müller et al. | 548/263.6 |
| 5,994,273 | A | | 11/1999 | Müller et al. | 504/273 |
| 6,121,204 | A | | 9/2000 | Müller et al. | 504/273 |
| 6,153,761 | A | | 11/2000 | Müller et al. | 548/263.6 |
| 6,251,831 | B1 | | 6/2001 | Müller et al. | 504/273 |
| 6,395,684 | B1 | * | 5/2002 | Feucht et al. | 504/273 |
| 6,525,211 | B1 | | 2/2003 | Müller et al. | 558/413 |
| 6,562,760 | B1 | * | 5/2003 | Feucht et al. | 504/273 |
| 6,656,883 | B1 | * | 12/2003 | Vogt et al. | 504/105 |
| 2001/0011063 | A1 | * | 8/2001 | Giencke et al. | 504/231 |
| 2004/0013678 | A1 | * | 1/2004 | Schnabel et al. | 424/184.1 |
| 2004/0052878 | A1 | * | 3/2004 | Baron et al. | 424/761 |
| 2004/0157743 | A1 | * | 8/2004 | Rosenfeldt et al. | 504/253 |

FOREIGN PATENT DOCUMENTS

| CA | 2201596 | 4/1996 |
|---|---|---|
| EP | 0 473 003 | 3/1992 |
| EP | 0 579 052 | 1/1994 |
| WO | 96/31121 | 10/1996 |
| WO | WO 9631121 A1 * | 10/1996 |
| WO | WO 9812923 A1 * | 4/1998 |

OTHER PUBLICATIONS

D. Stock et al: "Surfactant enhanced foliar uptake of some organic compounds: interactions with two model polyoxyethylene aliphatic alcohols." Pesticide Science, vol. 34, 1992, pp. 233-242, XP002240422.

* cited by examiner

*Primary Examiner*—Johann R Richter
*Assistant Examiner*—Danielle Sullivan
(74) *Attorney, Agent, or Firm*—Baker, Donelson, Bearman, Caldwell & Berkowitz, PC

(57) ABSTRACT

The invention relation to the use of alcohol ethoxylates of the formula (I)

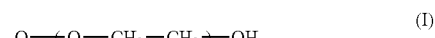

in which
n represents 4, 5, 6, 7 or 8 and
Q represents a branched tridecyl radical,
as penetrants for herbicidally active compounds from the group of the triazolinones. The invention also relates to corresponding plant treatment compositions and to their use in crop protection.

16 Claims, No Drawings

USE OF ALCOHOL ETHOXYLATES AS PENETRATION ENHANCERS

The present invention relates to the novel use of selected alcohol ethoxylates as penetrants for triazolinones having herbicidal properties.

It is generally known that many agrochemically active compounds, in particular those having systemic action, have to penetrate into the plant to be able to unfold their activity evenly throughout the plant. Thus, when the active compound is taken up via the leaves, the active compounds have to overcome the penetration barrier of the cuticle. Moreover, it is important that the agrochemically active compounds penetrate rapidly, distributed over a surface which is as large as possible, into the plant, since there may otherwise be the risk that the active components are washed off by rain.

Furthermore, it is generally known that some additives used in crop protection compositions, such as, for example, surfactants, mineral oils and vegetable oils, promote penetration of agrochemically active compounds into the plant and are thus able to enhance the activity of the active compounds. In specific cases, the additives may increase wettability, lead to a better distribution of the spray coating on the surface (=spreading) of the plant, increase the availability of the active compound in the dried-spray residue by partial dissolution or directly promote penetration of the active compound through the cuticle. Here, the additives are either incorporated directly into the formulation—which is only possible up to a certain percentage—or else added to the spray liquor in question using the tank-mix method.

Furthermore, it is already known that alcohol ethoxylates can be used as penetrants for numerous agrochemically active compounds (Gaskin, R. E. (1995), Adjuvants for agrochemicals, Proceedings of the 4th Int. Symp., Ch. 3, pp. 167-310, New Zealand Forest Research Institute Limited, Rotorua, New Zealand, (ISSN 0111-8129).

It has now been found that compounds of the formula (I)

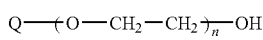
(I)

in which n represents 4, 5, 6, 7 or 8 and

Q represents a branched tridecyl radical, have surprisingly good suitability as penetrants for herbicidally active compounds from the group of the triazolinones. In commercial formulations, the compounds of the formula (I) are preferably present in concentrations of from 0.1 to 95% by weight. Here, the weight ratio of herbicidally active compound from the group of the triazolinones to alcohol ethoxylate of the formula (I) is preferably from 1:0.5 to 1:5.

In formula (I), Q represents in particular isotridecyl.

Accordingly, the invention relates to the use of alcohol ethoxylates of the formula (I) for the stated purpose. Moreover, the invention relates to plant treatment compositions comprising a combination consisting of a compound of the formula (I) and a triazolinone. Preference is given to plant treatment compositions comprising from 0.1 to 95% by weight of a compound of the formula (I), from 0.1 to 95% by weight of active compound from the group of the triazolinones, and from 4.9 to 80% by weight of additives.

It is extremely surprising that alcohol ethoxylates of the formula (I) are considerably more suitable as penetrants for herbicidally active triazolinones than comparable substances used for the same purpose. Accordingly, when using the plant treatment compositions according to the invention, the application rates of triazolinone can, surprisingly, be reduced considerably without any detrimental effect on the herbicidal action.

The use according to the invention of alcohol ethoxylates of the formula (I) has a number of advantages. Thus, these alcohol ethoxylates are products which can be handled without any problems and are available even in relatively large amounts. Moreover, they are biodegradable and permit the effectiveness of the application of triazolinones to be increased considerably.

Formula (I) provides a general definition of the alcohol ethoxylates which can be used according to the invention. The commercially available alcohol ethoxylates are generally mixtures of substances of the type having different chain lengths. Accordingly, the invention embraces all alcohol ethoxylates comprising an effective amount of isotridecyl ethoxylate having a degree of ethoxylation of 4, 5, 6, 7 or 8, in the amounts described.

Preference is given to alcohol ethoxylates of the formula (I) in which n represents 6.

The isotridecyl ethoxylates according to the invention having different degrees of ethoxylation can be self-manufactured. Examples of commercially available alcohol ethoxylates comprising the compounds of the formula (I) are the alcohol ethoxylates having a degree of ethoxylation of 6 which are commercially available under the names Lutensol® TO6 and Marlipal® 13/60.

The alcohol ethoxylates of the formula (I) and their use as surfactants are already known.

The herbicidally active compounds are preferably understood as including the compounds of the formula (II)

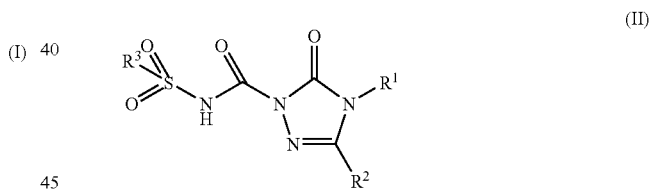
(II)

in which

R¹ represents hydrogen, hydroxyl, amino, $C_2$-$C_6$-alkylideneamino, represents in each case optionally cyano-, halogen- or $C_1$-$C_4$-alkoxy-substituted alkyl, alkenyl, alkynyl, alkoxy, alkenyloxy, alkylamino or dialkylamino having in each case up to 6 carbon atoms, represents in each case optionally cyano-, halogen- or $C_1$-$C_4$-alkyl-substituted cycloalkyl, cycloalkylalkyl or cycloalkylamino having in each case 3 to 6 carbon atoms in the cycloalkyl groups and, if appropriate, 1 to 4 carbon atoms in the alkyl moiety, or represents in each case optionally cyano-, nitro-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl or phenyl-$C_1$-$C_4$-alkyl, R² represents hydrogen, hydroxyl, mercapto, amino, cyano, halogen, represents in each case optionally cyano-, halogen- or $C_1$-$C_4$-alkoxy-substituted alkyl, alkoxy, alkylthio, alkylamino, dialkylamino, alkenyl, alkynyl, alkenyloxy, alkenylthio, alkynyloxy, alkynylthio, alkenylamino or alkynylamino having in each case up to 6 carbon atoms, represents in each case optionally cyano-, halogen- or $C_1$-$C_4$-alkyl-substituted cycloalkyl, cycloalkyloxy, cycloalkyl-thio, cycloalkylamino or cycloalkylalkyl having in each case 3 to 6 carbon atoms in the cycloalkyl groups and, if appropriate, 1 to 4 carbon atoms in the alkyl moiety, or represents in each case optionally cyano-, nitro-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, phenoxy, phenylthio, phenylamino or phenyl-$C_1$-$C_4$-alkyl, and $R^3$ represents phenyl which is optionally substituted by nitro, cyano, halogen, by in each case optionally cyano-, halogen- or $C_1$-$C_4$-alkoxy-substituted alkyl, alkylcarbonyl, alkoxy, alkoxycarbonyl, alkylthio, alkylsulphinyl, alkylsulphonyl, alkylamino, alkenyl, alkenyloxy, alkenylthio, alkenylamino, alkynyl, alkynyloxy, alkynylthio having in each case up to 6 carbon atoms, by in each case optionally cyano-, halogen- or $C_1$-$C_4$-alkyl-substituted cyclo-alkyl, cycloalkyloxy, cycloalkylthio, cycloalkylamino having in each case 3 to 6 carbon atoms in the cycloalkyl groups, or by in each case optionally cyano-, nitro-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, phenoxy, phenylthio, phenylsulphinyl, phenyl-sulphonyl or phenylamino.

For the radical definitions in formula (II), the following applies:

$R^1$ particularly preferably represents hydrogen, amino, or represents in each case optionally fluorine-, chlorine-, methoxy- or ethoxy-substituted methyl, ethyl, n- or i-propyl, ethenyl, propenyl, ethynyl, propynyl, methoxy, ethoxy, methyl-amino or ethylamino, represents dimethylamino, or represents optionally fluorine-, chlorine-, or methyl-substituted cyclopropyl.

$R^2$ particularly preferably represents hydrogen, chlorine, bromine, represents in each case optionally fluorine-, chlorine-, methoxy- or ethoxy-substituted methyl, ethyl, n- or i-propyl, n-, i- or s-butyl, methoxy, ethoxy, n- or i-propoxy, methylthio, ethylthio, n- or i-propylthio, methylamino, ethylamino, n- or i-propylamino, dimethylamino, diethylamino, ethenyl, propenyl, butenyl, ethynyl, propynyl, butynyl, propenyloxy, butenyloxy, propynyloxy, butynyloxy, propenylthio, butenylthio, propynylthio, butynylthio, propenylamino, butenylamino, propynylamino or butynylamino, or represents in each case optionally fluorine-, chlorine- or methyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl or cyclohexylmethyl.

$R^3$ very particularly preferably represents phenyl which is substituted by nitro, cyano, fluorine, chlorine, bromine, by in each case optionally fluorine-, chlorine-, methoxy- or ethoxy-substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl, by in each case optionally fluorine-, chlorine- or methyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio or cyclohexylthio, or by in each case optionally cyano-, nitro-, fluorine-, chlorine-, bromine-, methyl-, ethyl-, n- or i-propyl-, n-, i-, s- or t-butyl-, trifluoromethyl-, methoxyethoxy-, n- or i-propoxy-, difluoromethoxy- or trifluoromethoxy-substituted phenyl, phenoxy, phenylthio, phenylsulphinyl or phenylsulphonyl.

Instead of the pure active compounds of the formula (II), it is also possible to use salts of the compounds of the formula (II) with metals and/or with basic nitrogen compounds in the active compound combinations according to the invention.

Here, preference is given to salts of the compounds of the formula (II) with alkali metals, such as, for example, lithium, sodium, potassium, rubidium or caesium, with particular preference with sodium or potassium, with alkaline earth metals, such as, for example, magnesium, calcium or barium, with particular preference with calcium, or with earth metals, such as, for example, aluminium.

In the present context, herbicidally active triazolinones are most preferably to be understood as meaning the following substances:

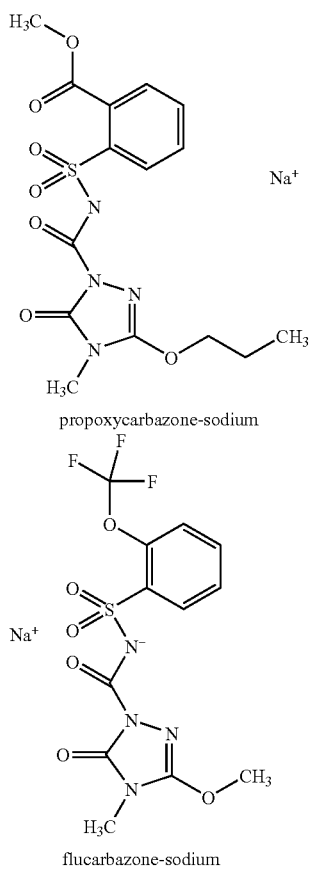

propoxycarbazone-sodium flucarbazone-sodium

All of the substances mentioned above and their use as herbicides are known (cf. EP-A-341489, EP-A-422469, EP-A-425948, EP-A-431291, EP-A-507171, EP-A-534266, WO-A-96/11188, WO-A-96/27590, WO-A-96/27591, WO-A-97/03056, U.S. Pat. No. 5,534,177).

Suitable additives which may be contained in the plant treatment compositions according to the invention are further agrochemically active compounds, and crystallization inhibitors, wetting agents, emulsifiers and also water.

Suitable agrochemically active compounds are preferably substances having insecticidal, acaricidal, nematicidal, fungicidal and in particular herbicidal properties. However, it is also possible to add bird repellents, plant nutrients and soil improvers. Mention may also be made of the possible addition of compounds which improve compatibility with crop plants (safeners), as a further preferred embodiment of the crop treatment compositions according to the invention.

Such agrochemically active compounds having herbicidal properties are, for example: amidosulphuron, bentazone, bromoxynil, carfentrazone(-ethyl), cinidon-(ethyl), clodinafop(-propargyl), clopyralid, chlorsulphuron, chlortoluron, cyclosulphamuron, 2,4-D, diclofop(-methyl), difenzoquat, diflufenican, florasulam, flupyr-sulphuron(-methyl, -sodium), pyraflufen(-ethyl), ethoxyfen, fenoxaprop(-ethyl), fluoroglycofen(-ethyl), flupropacil, fluroxypyr, iodosulphuron, isoproturon, meco-prop, metosulam, metribuzin, metsulphuron(-methyl), pendimethalin, prosulphocarb, pyridate, sulphosulphuron, thifensulphuron(-methyl), tralkoxydim, triasulphuron, tri-benuron(-methyl), trifluralin.

Safeners that may be emphasized are cloquintocet-mexyl, fenchlorazol-ethyl, mefenpyr-diethyl, furilazole and dymron.

Suitable crystallization inhibitors which may be present in the plant treatment compositions according to the invention are all substances which may customarily be used in agrochemical compositions for such purposes. By way of preference, mention may be made of N-alkylpyrrolidones, such as N-octylpyrrolidone and N-dodecylpyrrolidone, furthermore of copolymers of polyvinyl-pyrrolidone and polyvinyl alcohol, such as, for example, the polyvinylpyrrolidone/polyvinyl alcohol copolymer known under the name Luviskol VA 64 (from BASF), furthermore N,N-dimethyl-alkylcarboxamides, such as N,N-dimethyl-decanamide or the N,N-dimethyl-$C_{6-12}$-alkanecarboxamide mixture known under the name Hallcomid® (from Hall Comp.), and furthermore copolymers of ethylenediamine with ethylene oxide and propylene oxide, such as, for example, the product known under the name Synperonic T 304 (from Uniqema).

Suitable wetting agents are all substances which may be customarily used for such purposes in plant treatment compositions. By way of preference, mention may be made of alkylphenol ethoxylates, dialkylsulphosuccinates, such as dioctylsulphosuccinate sodium, lauryl ether sulphates and polyoxyethylene sorbitan fatty acid ester.

Suitable emulsifiers are all customary nonionic, anionic, cationic and zwitterionic substances having surface-active properties which are customarily used in agrochemical compositions. These substances include reaction products of fatty acids, fatty acid esters, fatty alcohols, fatty amines, alkylphenols or alkylarylphenols with ethylene oxide and/or propylene oxide, and their sulphuric acid esters, phosphoric acid monoesters and phosphoric acid diesters, furthermore reaction products of ethylene oxide with propylene oxide, and additionally alkylsulphonates, alkyl sulphates, aryl sulphates, tetraalkylammonium halides, trialkylarylammonium halides and alkylaminesulphonates. The emulsifiers can be used individually or else in mixtures. By way of preference, mention may be made of reaction products of castor oil with ethylene oxide in a molar ratio of from 1:20 to 1:60, reaction products of $C_6$-$C_{20}$-alcohols with ethylene oxide, propylene oxide or butylene oxide or with mixtures of two or three of these alkene oxides in a molar ratio of 1:5 to 1:50, reaction products of fatty amines with ethylene oxide in a molar ratio of from 1:2 to 1:25, reaction products of fatty amines with ethylene oxide/propylene oxide mixtures in a molar ratio of from 1:2 to 1:20, reaction products of 1 mol of phenol with 2 to 3 mol of styrene and 10 to 50 mol of ethylene oxide, reaction products of $C_8$-$C_{12}$-alkyl-phenols with ethylene oxide in a molar ratio of from 1:5 to 1:30, alkylglycosides, $C_8$-$C_{16}$-alkylbenzenesulphonic acid salts, such as, for example, calcium, monoethanolammonium, diethanolammonium and triethanolammonium salts.

Examples of nonionic emulsifiers which may be mentioned are the products known under the names Pluronic PE 10 100 (from BASF) and Atlox 4913 (from Uniqema). Also suitable are tristyrylphenyl ethoxylates. Examples of anionic emulsifiers which may be mentioned are the commercial product from Bayer AG which is known under the name Baykanol SL (=condensate of sulphonated ditolyl ether with formaldehyde), and also phosphated or sulphated tristyrylphenol ethoxylates, especially Soprophor SLK and Soprophor 4D 384 (from Rhodia).

When alcohol ethoxylates of the formula (I) are used according to the invention, the content of these products can be varied within a certain range. In general, alcohol ethoxylates of the formula (I) are used in such an amount that they are present in the commercial formulations in concentrations of from 0.1 to 30% by weight, preferably from 5 to 15% by weight. Here, the weight ratio of herbicidally active compound from the group of the triazolinones to alcohol ethoxylate of the formula (I) is preferably chosen such that it is generally from 1:0.2 to 1:20 and particularly preferably from 1:0.5 to 1:5.

The content of the individual components in the plant treatment compositions according to the invention can be varied within a certain range. Preference is given to plant treatment compositions in which the content of a compound of the formula (I) is from 0.5 to 40% by weight, of active compound from the group of the triazolinones is from 2.5 to 70% by weight, and of additives is from 5 to 50% by weight.

If the plant treatment compositions according to the invention are ready-to-use products, preference is given to those in which the content of a compound of the formula (I) is from 0.02 to 0.25% by weight, of active compound from the group of the triazolinones is from 0.01 to 2% by weight, preferably from 0.1 to 2% by weight, and of additives is from 0 to 99% by weight.

Preferably, the ready-to-use products comprise at least 0.05% by weight and most preferably at least 0.1% by weight of a compound of the formula (I).

The ready-to-use plant treatment compositions are preferably a spray liquor which is customarily used in crop protection and prepared by the tank-mix process.

The plant treatment compositions according to the invention are prepared by mixing the components with each other in the ratios desired in each case. In general, an active compound from the group of the triazolinones is initially charged, and the other components are then added with stirring, in any order.

When preparing the plant treatment compositions according to the invention, the temperatures can be varied within a certain range. In general, the compositions are prepared at temperatures from 10° C. to 50° C., preferably at room temperature.

Suitable for preparing plant treatment compositions according to the invention are apparatus customarily used for preparing agrochemical formulations.

The plant treatment compositions according to the invention can be applied either as such or after prior dilution with water or other diluents, i.e., for example, as ready-to-use solutions, suspensions, emulsions, powders, pastes and granules. Application is carried out by customary methods, for example by watering, spraying, atomizing or spreading.

The plant treatment compositions according to the invention can be applied both before and after emergence of the plants. They can also be incorporated into the soil prior to sowing.

The application rate used can be varied within a relatively wide range. It depends substantially on the nature of the desired effect. In general, the application rates are from 1 g to 1 kg of active compound per hectare of soil surface, preferably from 5 g to 0.5 kg per ha.

With the aid of the plant treatment compositions according to the invention, it is possible to apply triazolinones in a particularly advantageous manner to the plants and/or their habitat. Here, the tendency of solid active compounds to crystallize is reduced, the penetration power of the active compounds is enhanced and, compared to customary formulations, the biological activity of the active components is increased.

The invention is illustrated by the examples below.

PREPARATION EXAMPLE

Example of a Plant Treatment Composition According to the Invention

The composition comprises 18.0% by weight of propoxycarbazone-sodium 30.0% by weight of Marlipal® 013/60 or Lutensol® TO 6

9.0% by weight of Atlas® G 1087

6.0% by weight of SCS 2793 (castor oil ethoxylate)

3.0% by weight of Atlox® LP-6

0.2% by weight of butylhydroxytoluene 0.5% by weight of Aerosil® 200 V 8.0% by weight of castor oil IF 25.3% by weight of sunflower oil

USE EXAMPLE

Determination of the penetration of triazolinones into barley plants.

Preparation of Active Compound

To prepare a ready-to-use preparation of active compound, in each case radiolabelled active compound (propoxycarbazone-sodium) was diluted with unlabelled active compound of industrial quality and with such an amount of water that a spray liquor containing 100 mg propoxycarbazone-sodium per litre was formed. Accordingly, the additives were tested in a tank-mix in a concentration of 0.1% by weight.

Application Rate

Per plant, in each case 3 µl of ready-to-use preparation of active compound and a defined, in each case identical amount of radiolabelled propoxycarbazone-sodium were used.

Plants

The plants used were 14 day-old barley plants of the cultivar Tapir which had been grown in vermiculite and were in the 2-leaf stage.

Point of Application

3 µl of the ready-to-use preparation of active compound were in each case applied onto the first leaf, at a distance of 5.5 cm to the tip of the leaf.

Duration of the Experiment 24 hours from the time of application to the removal by washing.

Repetitions 5 repetitions per preparation of active compound.

Climate 12 hours of light at 22-23° C. and 55-60% relative atmospheric humidity; 10 hours of darkness at 15° C. and 80% relative atmospheric humidity, and twice 1 hour each of twilight at the same climate as in the period before.

Controls

In each case 3 µl of ready-to-use preparation of active compound were pipetted directly into a scintillation bottle. 5 repetitions per preparation of active compound.

Preparation

The second leaves of the barley plants at the 2-leaf stage, freshly grown in a greenhouse, were cut off. The remaining leaves of the horizontally arranged plants were then fixed with the aid of microscope slides such that the points of application on the leaves in an area of 2 cm were not twisted. Following their preparation, the ready-to-use preparations of active compound were stirred at room temperature for 60 minutes.

Application and Work-Up

In each case 3 µl of the preparation of active compound were applied onto the middle of a leaf. The plants were then allowed to rest until the preparation of active compound had dried on. At the same time, as a control, in each case 3 µl of the preparation of active compound were pipetted directly into a scintillation bottle. This control was carried out in 5 repetitions. Immediately afterwards, the other preparations of active compounds and plants were subjected to the same procedure. Following application, a temperature of 21-22° C. and a relative atmospheric humidity of 70% was maintained in the laboratory.

After all of the preparations of active compounds that had been applied had dried on, the treated plants were placed in a climatized chamber for 22 hours. 24 hours after the application of the preparations of active compounds, the leaves of all plants were once more fixed using slides. The entire surface of the point of application was then covered with 30 µl of a 5% strength solution of cellulose acetate in acetone. After the solution had dried on completely, the cellulose acetate film formed was in each case removed and placed into a scintillation bottle. In each case, 1 ml of acetone was then added to the cellulose acetate film. The samples remained at room temperature in closed vessels until the substance contained therein had been dissolved. Thereafter, in each case 2 ml of scintillation liquid were added. Beforehand, the tips of the leaves had been cut off in one piece and placed into cardboard hats. Cardboard hats and content were dried at 50° C. for 16 hours. The radioactivity of all samples was then determined by liquid and incineration scintillation. The values obtained are used to calculate the percentage of uptake of active compound and translocation. 0% means that no active compound has been taken up and translocated; 100% means that all of the active compound has been taken up and translocated.

The test results are shown in the table below.

TABLE I

Determination of the penetration of propoxycarbazone-sodium into barley plants

| Surfactant | Chemically active compounds | Uptake (% of radio activity applied) |
|---|---|---|
| Marlipal ® 13/60 | isotridecyl ethoxylate 6EO | 15.70 |
| Lutensol ® TO6 | isotridecyl ethoxylate 6EO | 19.90 |
| Trend ® | nonylphenol ethoxylate | 6.94 |
| Armoblen ® | tallow amine alkoxylate | 2.42 |

TABLE I-continued

Determination of the penetration of propoxycarbazone-sodium into barley plants

| Surfactant | Chemically active compounds | Uptake (% of radio activity applied) |
|---|---|---|
| Atplus ® MBA 1304 | monobranched alcohol alkoxylate | 2.0 |
| Hasten ® | rapeseed oil ethyl ester + NIS | 1.75 |
| Euro Dash ® | mineral oil + emulsifier | 1.55 |
| Agrocer ® 04 | montan wax emulsion with emulsifier | 1.15 |
| Eumulgin ® ME3518 | rapeseed oil methyl ester + emulsifier | 1.09 |
| Without additive | (tap water) | 0.25 |

The results show that the formulation according to the invention penetrates considerably better than the formulations used for comparisons.

The invention claimed is:

1. A method for improving the penetration of a herbicidally active triazolinone into a plant comprising:
applying to a plant and/or a habitat of said plant, a penetrant compound comprising an alcohol ethoxylate represented by the formula (I)

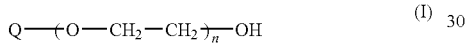
(I)

in which
n represents 6 and
Q represents a branched tridecyl radical,
and one or more herbicidally active triazolinones.

2. The method according to claim 1 wherein Q is isotridecyl.

3. The method according to claim 2, wherein said triazolinone is flucarbazone-sodium or propoxycarbazone-sodium.

4. A herbicidally active formulation comprising:
a) an alcohol ethoxylate penetration enhancing compound represented by the formula (I)

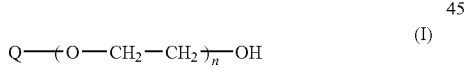
(I)

in which
n represents 6 and
Q represents a branched tridecyl radical, and
b) one or more herbicidally active triazolinones,
wherein said compound of the formula (I) is present in a concentration of from 0.1 to 95% by weight.

5. The formulation of claim 4 wherein the weight ratio of said one or more triazolinones to said compound of the formula (I) is from 1:0.5 to 1:5.

6. The formulation according to claim 5 wherein said triazolinone is flucarbazone-sodium or propoxycarbazone-sodium.

7. The formulation according to claim 4 to 6 wherein Q is isotridecyl.

8. A method for treating plants comprising applying the herbicidally active formulation according to claim 4 to plants, or their habitats, or both.

9. A plant treatment composition comprising:
a) an alcohol ethoxylate represented by the formula (I)

(I)

in which
n represents 6 and
Q represents a branched tridecyl radical, and
b) one or more triazolinones.

10. The plant treatment composition of claim 9 wherein Q is isotridecyl and said triazolinone is flucarbazone-sodium or propoxycarbazone-sodium.

11. The plant treatment composition according to either of claim 9 or 10 comprising:
a) from 0.1 to 95% by weight of the compound of the formula (I),
b) from 0.1 to 95% by weight of said triazolinone, and
c) from 4.9 to 80% by weight of one or more additives.

12. The plant treatment composition according to claim 9 wherein
a) the content of the compound of the formula (I) is from 0.5 to 40% by weight,
b) the content of said one or more triazolinones is from 2.5 to 70% by weight, and
c) the content of said additives is from 5 to 50% by weight.

13. A method for treating plants comprising applying the plant treatment composition according to claim 9 to plants, or their habitats, or both.

14. A ready-to-use plant treatment composition comprising
a) of a compound of the formula (I)

(I)

in which
n represents 6 and
Q represents a branched tridecyl radical in the range of from 0.02 to 0.25% by weight,
b) a herbicidally active triazolinone in the range from 0.01 to 2% by weight, and
c) one or more additives in the range from 0% to 99% by weight.

15. The ready-to-use plant treatment composition according to claim 14 wherein said plant treatment composition is in the form of a spray liquor prepared by a tank-mix method.

16. A method for treating plants comprising applying the penetrating compound according to claim 1 to plants, or their habitats, or both.

* * * * *